(12) United States Patent
Parrott et al.

(10) Patent No.: US 7,670,382 B2
(45) Date of Patent: Mar. 2, 2010

(54) EXTENDED ARTICULAR SURFACE RESURFACING HEAD

(75) Inventors: Russell Parrott, Winona Lake, IN (US); Nathan A Winslow, Warsaw, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 1147 days.

(21) Appl. No.: 11/258,341

(22) Filed: Oct. 25, 2005

(65) Prior Publication Data

US 2006/0036328 A1 Feb. 16, 2006

Related U.S. Application Data

(63) Continuation-in-part of application No. 10/669,971, filed on Sep. 24, 2003, now Pat. No. 7,585,327.

(51) Int. Cl.
*A61F 2/40* (2006.01)
(52) U.S. Cl. ............... 623/19.14; 623/19.11; 623/23.42
(58) Field of Classification Search ... 623/19.11–19.14, 623/23.42
See application file for complete search history.

(56) References Cited

U.S. PATENT DOCUMENTS

| 3,979,778 | A |   | 9/1976  | Stroot et al. |
|-----------|---|---|---------|---------------|
| 4,042,980 | A |   | 8/1977  | Swanson et al. |
| 4,261,062 | A | * | 4/1981  | Amstutz et al. .......... 623/19.13 |
| 4,328,593 | A |   | 5/1982  | Sutter et al. |
| 4,470,158 | A |   | 9/1984  | Pappas et al. |
| 4,550,450 | A |   | 11/1985 | Kinnett |
| 4,919,670 | A |   | 4/1990  | Dale et al. |
| 5,314,479 | A |   | 5/1994  | Rockwood, Jr. et al. |
| 5,358,526 | A |   | 10/1994 | Tornier |
| 5,549,682 | A |   | 8/1996  | Roy |
| 5,910,171 | A |   | 6/1999  | Kummer et al. |
| 6,045,582 | A |   | 4/2000  | Prybyla |
| 6,120,542 | A |   | 9/2000  | Camino et al. |
| 6,129,764 | A |   | 10/2000 | Servidio |
| 6,197,062 | B1 |  | 3/2001  | Fenlin |
| 6,197,063 | B1 |  | 3/2001  | Dews |
| 6,589,282 | B2 |  | 7/2003  | Pearl |
| 6,620,197 | B2 |  | 9/2003  | Maroney et al. |

(Continued)

FOREIGN PATENT DOCUMENTS

| DE | 42 20 217 | 12/1993 |
|----|-----------|---------|
| EP | 0 617 934 | 10/1994 |
| EP | 0 845 250 | 6/1998  |
| EP | 1 064 890 | 1/2001  |
| EP | 1 464 305 | 10/2004 |
| FR | 2 578 739 | 9/1986  |
| FR | 2880793   | 7/2006  |

OTHER PUBLICATIONS

"Copeland Humeral Resurfacing Head", Biomet Orthopedics, Inc., copyright 2001.

(Continued)

*Primary Examiner*—David H Willse
*Assistant Examiner*—Javier G Blanco
(74) *Attorney, Agent, or Firm*—Harness, Dickey & Pierce, P.L.C.

(57) ABSTRACT

A resurfacing implant comprising a head and an extended articulating surface protruding from a portion of the head operable to articulate with at least one of a bone and a ligament. The head has an exterior articulating surface, an interior surface opposite the exterior articulating surface, and an anchoring device extending from the interior surface.

14 Claims, 13 Drawing Sheets

U.S. PATENT DOCUMENTS

| | | |
|---|---|---|
| 6,673,114 B2 | 1/2004 | Hartdegen et al. |
| 6,783,549 B1 | 8/2004 | Stone et al. |
| 2001/0047210 A1 | 11/2001 | Wolf |
| 2002/0022889 A1 | 2/2002 | Chibrac et al. |
| 2002/0099381 A1 | 7/2002 | Maroney |
| 2002/0099445 A1 | 7/2002 | Maroney et al. |
| 2003/0028253 A1 | 2/2003 | Stone et al. |
| 2003/0144738 A1 | 7/2003 | Rogalski |
| 2004/0002765 A1 | 1/2004 | Maroney et al. |
| 2004/0034431 A1 | 2/2004 | Maroney et al. |
| 2004/0193277 A1 | 9/2004 | Long et al. |
| 2004/0193278 A1 | 9/2004 | Maroney et al. |
| 2005/0021038 A1 | 1/2005 | Maroney |
| 2005/0065612 A1 | 3/2005 | Winslow |
| 2007/0198094 A1 | 8/2007 | Berelsman et al. |

OTHER PUBLICATIONS

"Global Advantage CTA Humeral Head," Depuy Orthopaedics, copyright 2000 (2 pages).

Two engineering drawings illustrating a humeral head replacement device.

* cited by examiner

EXTENDED ARTICULAR SURFACE RESURFACING HEAD

CROSS-REFERENCE TO RELATED APPLICATIONS

This application is a continuation-in-part application of U.S. patent application Ser. No. 10/669,971 filed on Sep. 24, 2003. The disclosure of the above application is incorporated herein by reference.

FIELD OF THE INVENTION

The present invention relates to prosthetic implants. In particular, the present invention relates to a humeral resurfacing implant.

BACKGROUND OF THE INVENTION

The humerus is the longest and largest bone of the human upper extremity. It is divisible into a body and two extremities. The upper extremity comprises a head that is joined to the body by a constricted portion generally called the neck. The head is nearly hemispherical in form and articulates with the glenoid cavity of the scapula or shoulder blade. The humerus is secured to the scapula by the rotator cuff muscles and tendons.

It is not uncommon for the exterior surface of the humeral head to be damaged or defective. Conventionally, a variety of humeral head resurfacing implants exist for repairing humeral head surfaces. While conventional humeral head resurfacing implants are suitable for their intended uses, such implants are subject to improvement.

Conventional humeral head resurfacing implants fail to accommodate patients having inadequate rotator cuff muscles. Specifically, conventional implants do not permit articulation between the implant and the concave undersurface of the coracoacromial arch of the scapula, the coracoacromial arch being a structural component of the shoulder comprising the coracoacromial ligament, coracoid process, and acromion. Thus, there is a need for a humeral head resurfacing implant that permits articulation with the coracoacromial arch in patients having inadequate rotator cuff muscles.

SUMMARY OF THE INVENTION

In one embodiment, the present invention provides for a resurfacing implant comprising a head and an extended articulating surface protruding from a portion of the head operable to articulate with at least one of a bone and a ligament. The head has an exterior articulating surface, an interior surface opposite the exterior articulating surface, and an anchoring device extending from the interior surface.

In another embodiment, the present invention provides for a humeral head resurfacing implant comprising a humeral head having an articulating surface, an engagement stem extending from the head, and an extended surface protruding from the head operable to articulate with at least one element of a coracoacromial arch.

In yet another embodiment, the present invention provides for a method for resurfacing a humeral head of an implant site. The method comprises preparing the humeral head and implanting an implant at the humeral head. The implant has an exterior articulating surface, an interior surface opposite the exterior surface, a stem extending from the interior surface, and an extended articulating surface operable to articulate with at least one element of a coracoacromial arch.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiments is merely exemplary in nature and is in no way intended to limit the invention, its application, or uses.

Figure 1:
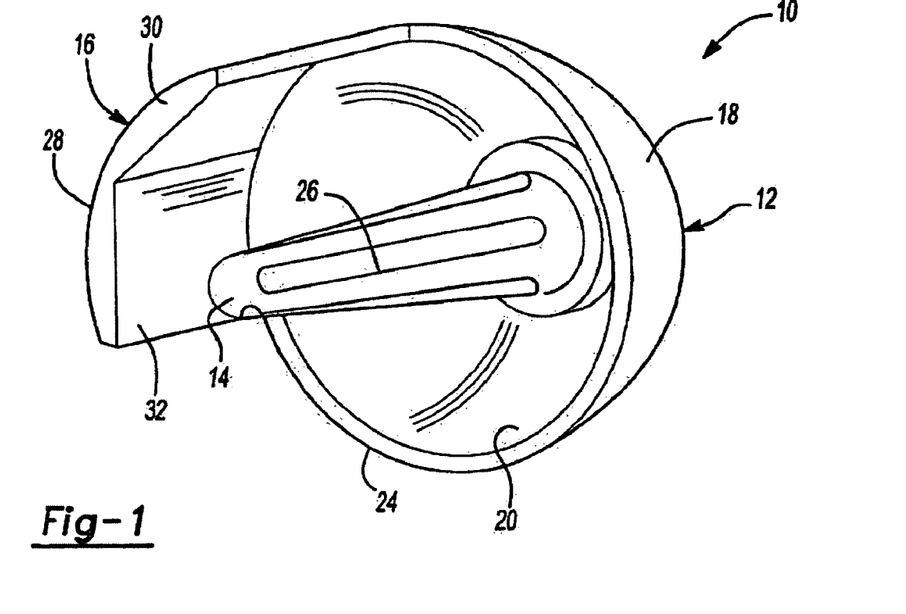
FIG. 1 is a perspective view of an implant according to the present invention.
Figure 2:
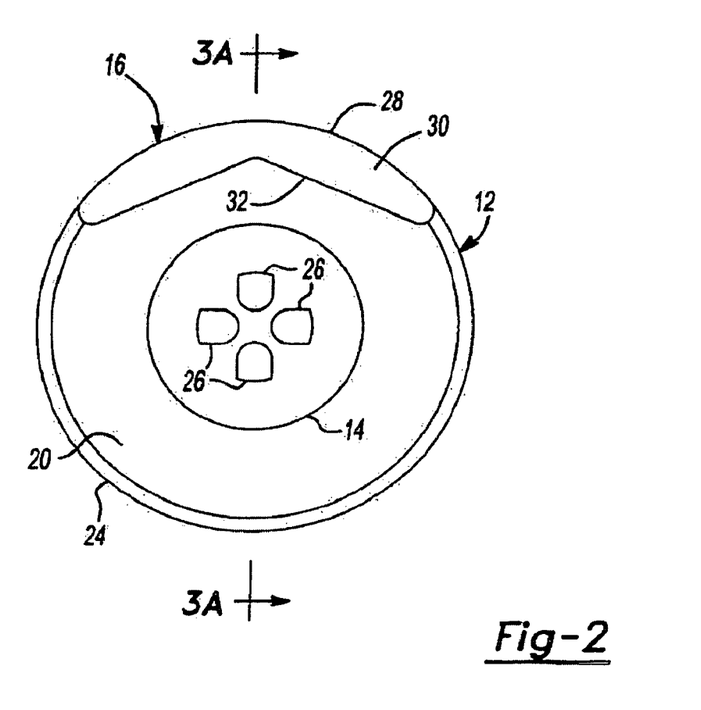
FIG. 2 is bottom view of the implant of FIG. 1.
Figure 3A:
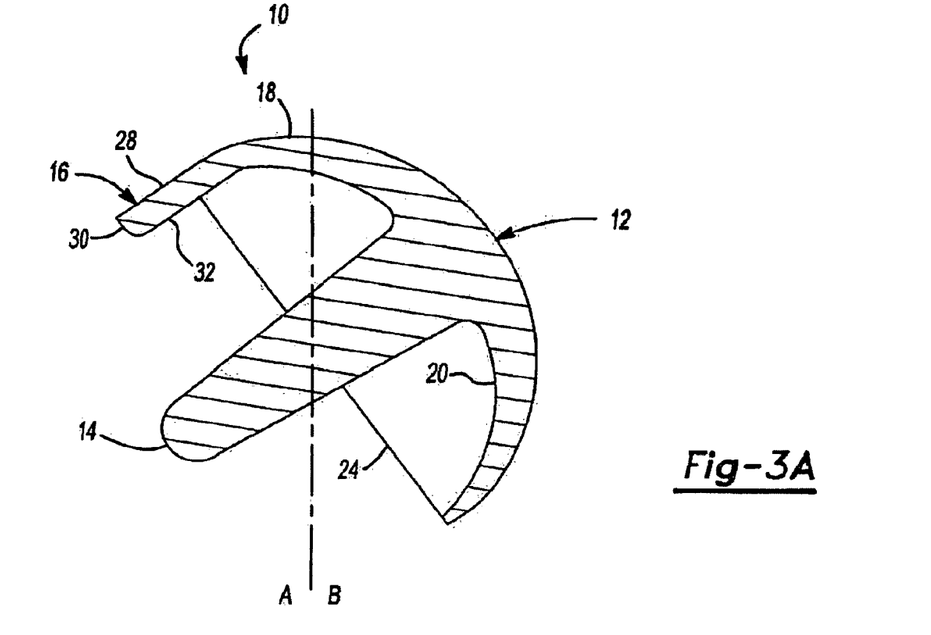
FIG. 3A is a cross-sectional view taken along line 3-3 of FIG. 2.
Figure 3B:
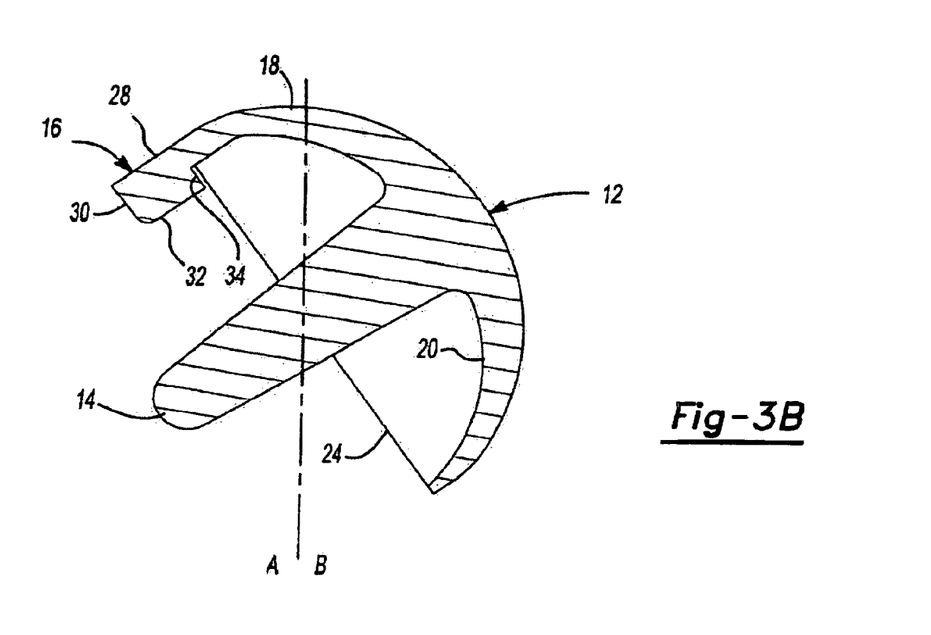
FIG. 3B is a cross-sectional side view of the implant of the present invention according to an additional embodiment.

With initial reference to FIGS. 1 through 3, a resurfacing implant according to the present invention is illustrated and identified at reference numeral 10. The implant 10 is typically divided into, as illustrated in FIG. 3, a lateral region A and a medial region B, which is in relation to the implant position in the patient. The implant 10 generally includes a resurfacing head 12, an anchoring device or stem 14, and an extended surface 16. The extended surface 16 may be located in the lateral region A, as illustrated, or at any other position about a periphery of the head 12. The head 12 includes an exterior surface 18 and an interior surface 20 opposite the exterior surface 18. The exterior surface 18 is generally convex, or dome-shaped, and smooth. The interior surface 20 is generally concave.

The interior surface 20 is also generally dome-shaped and substantially mirrors the exterior surface 18. The interior surface 20 is generally concave. The interior surface 20 may be smooth or may include features, such as pores or coatings that facilitate bonding of the interior surface 20 to a resurfaced implant site. The interior surface 20 may be bonded to the implant site with or without bone cement. The interior surface 20 optionally terminates at an annular rim 24.

The stem 14 extends from the interior surface 20. The stem 14 may optionally be tapered such that the diameter of the stem 14 is at its greatest at the interior surface 20. To facilitate cooperation between the stem 14 and the implant site, the stem 14 may optionally include one or more details, such as flutes 26. In addition to or in place of flutes 26, the stem 14 may include surface features, such as pores or coatings, to enhance the creation of a bond between the stem 14 and the implant site.

In some applications, the extended surface 16 is located in the lateral region A to engage a surface or bone, such as at least one portion of the coracoacromial arch. However, the extended surface 16 may be located at any other position about the rim 24 to engage a variety of different bones and/or ligaments. The extended surface 16 is generally comprised of an outer surface 28, a base surface 30, and an inner surface 32. The outer surface 28 is typically a continuation of the exterior surface 18. The outer surface 28 may be of any suitable shape or configuration, however, in many instances, the outer surface 28 is curved or rounded to follow the general shape of the exterior surface 18. The outer surface 28 extends about a portion, but less than an entirety of the annular rim 24. The extended surface 16 generally extends beyond an equator of the hemispherical head 12, which is generally defined by the rim 24. As seen in FIG. 3A, the extended surface 16 extends from the head 12 in a planar and/or cylindrical manner.

The base surface 30 generally extends from the outer surface 28 toward the stem 14 at approximately a right angle to the outer surface 28. The base surface 30 may be generally planar or may include various surface features to enhance interaction between the base surface 30 and the implantation site. The base surface 30 is typically shaped to accommodate the curvature of the annular rim 24. The length of the base surface 30 determines, in part, the width of the extended surface 16.

The inner surface 32 extends from the base surface 30 toward the interior surface 20. The inner surface 32 extends from the base surface 30 at an approximate right angle to the base surface 30. The inner surface 32 may be of any suitable shape but is typically shaped to generally accommodate the curvature of the annular rim 24. In some applications, the inner surface 32 may be wedged shaped, typically in the shape of a "V", to generally facilitate interaction between the implant 10 and the implantation site by providing a surface that matches the shape of a prepared bone that is to receive the implant 10. The shape of the inner surface 32, such as the wedge shape, may be used to act as a further aide to maintain the implant 10 in its desired position and prevent rotation of the implant 10 at the implantation site.

If the extended surface 16 is of a relatively small width, the inner surface 32 may be an extension of the interior surface 20 (FIG. 3A). As illustrated in FIG. 3B, if the extended surface 16 is of a relatively large width, the inner surface 32 is not a continuation of the interior surface 20, but is connected to the interior surface 20 by an upper surface 34. The upper surface 34 runs generally parallel to the base surface 30 and may be, for example, planar or curved. The upper surface 34 forms a step on the extended surface 16.

The implant 10 may be made of any suitable biocompatible material, but is typically made from a metal such as cobalt chrome or titanium. The interior surface 20 may be coated with a suitable material, such as titanium plasma spray or hydroxyapatite, to enhance the adhesion of the interior surface 20 to the implantation site or to enhance the effectiveness of any material, such as bone cement, that may be used to affix the interior surface 20 to the implantation site. The stem 14 may optionally be provided with a blasted finish, with or without hydroxyapatite, or a micro-bond finish, with or without hydroxyapatite. As a further option, bone cement may be used as an aide to retain the implant 10 in position.

The implant 10 may be of various different sizes and dimensions depending on the sizes and dimensions of the implant site. For example, to accommodate patients having large humeral heads, the implant 10 may be of a greater overall size than that required to accommodate patients having smaller humeral heads. Further, the shape of the exterior surface 18 may be customized to insure proper articulation at the implant site. Implants 10 of various different shapes and sizes may be packaged together and sold in a single kit.

Figure 4:
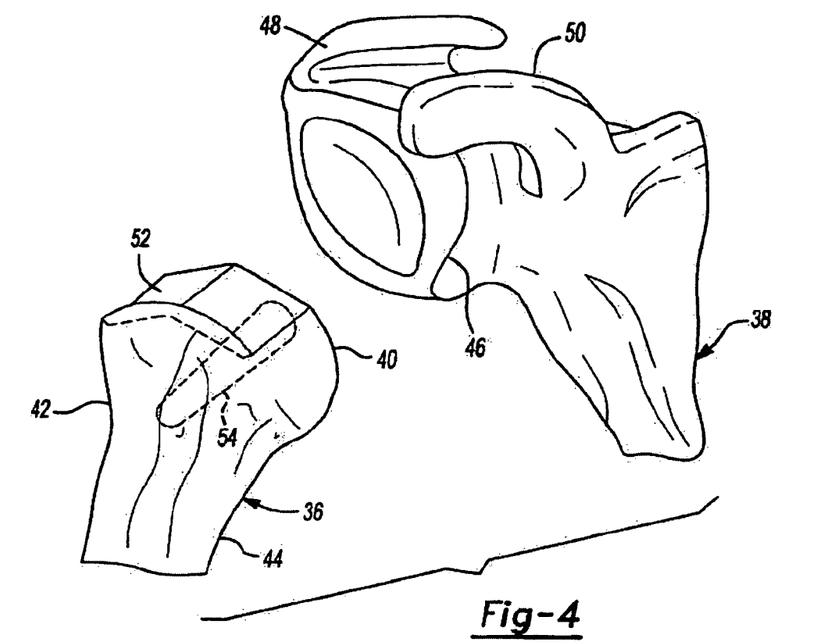
FIG. 4 is a perspective view of a typical implantation site prepared to receive the implant of FIG. 1.
Figure 5:
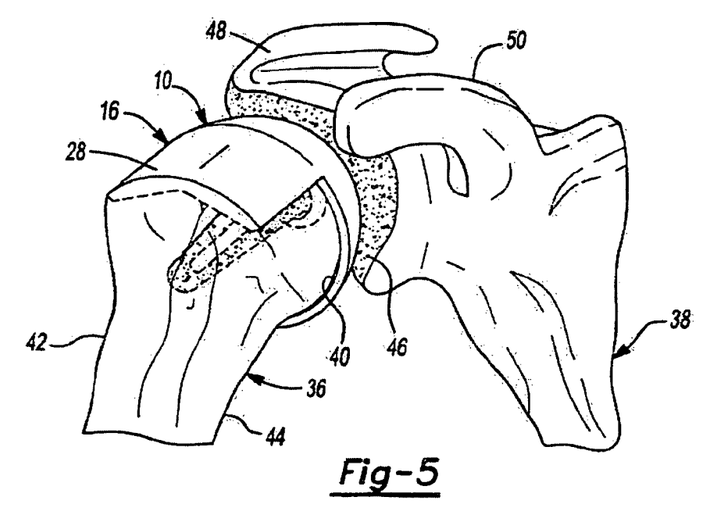
FIG. 5 is a perspective view of the implant of FIG. 1 implanted at the implantation site of FIG. 4.

With reference to FIGS. 4 and 5, the implantation and operation of the implant 10 will be described in detail. While the implant 10 is generally described as a humeral head resurfacing implant, it must be noted that the implant 10 may be used in a variety of different applications. The implantation site generally includes a humerus 36 and a shoulder blade or scapula 38. The humerus 36 is generally comprised of a head 40, a neck 42, and a stem 44. The scapula 38 is generally comprised of a glenoid cavity 46 that receives the head 40, a coracoacromial arch 48, and a coracoid process 50.

To receive the implant 10, a portion of the exterior surface of the humeral head 40 is resurfaced and/or removed to accommodate the resurfacing head 12 of the implant 10 such that, when implanted, the implant head 12 does not generally increase the overall dimensions of the humeral head 40. The head 12 is further resected at 52 to accommodate the extended surface 16. This resection at 52 may be performed with or without the use of a resection jig. To minimize bone loss, the resection at 52 often takes the shape of a "V", however, the resection 52 may be of various other shapes or configurations. The "V" shape may also prevent rotation of the head 12, even though the interaction between the stem 14 and the implant site is more than adequate to secure the head 12 into position.

To receive the stem 14, which is generally referred to as a short stem 14, a peg hole 54 is formed within the head 40 using conventional instruments and techniques. The hole 54 is formed with dimensions substantially similar to the dimensions of the stem 14 and is positioned such that when the stem 14 is seated within the hole 54, the exterior surface 18 closely approximates the outer surface of the humeral head 40. The hole 54 extends generally only through a portion of the humeral head 40 and does not necessarily extend to the stem 44 or within the intramedullary canal of the humerus. To ensure proper placement of the implant 10, a trial implant (not shown) may be positioned at the implantation site before the implant 10 is implanted.

The trial implant is substantially similar to the implant 10. A stem of the trial implant is placed within the hole 54 and the shoulder joint is reduced. If necessary, the head 40 is reamed to better approximate the size and shape of the interior surface 20. After the proper position of the trial implant is noted, the trial is removed and the stem 14 of the implant 10 is seated within the hole 54. The implant 10 is then positioned such that it is in substantially the same position as the trial implant. The particular size of the implant 10 is chosen according to the size and dimensions of the patient's humeral head 40 and scapula 38. It must be noted that typically the stem 14 only extends through a portion of the head 40 and does not enter, or replace, the natural stem 44 of the humerus 36.

As illustrated in FIG. 5, the implant 10 is orientated at the humeral head 40 such that the extended surface 16 is positioned at or near the coracoacromial arch 48. The extended surface 16 may either abut, or closely abut, the coracoacromial arch 48. When the patient's rotator cuff muscles are inadequate, the extended surface 16 typically contacts the coracoacromial arch to provide metal on bone articulation with the coracoacromial arch 48. However, the extended surface 16 may be rotated to any other position to engage other bones, ligaments, or surfaces other than, or in addition to, the coracoacromial arch 48.

While interaction between the stem 14 and the hole 54 is typically suitable to secure the implant 10 within the hole 54, the stem 14 may optionally be secured within the hole 54 using a suitable adhesive, such as bone cement 56. The optional bone cement 56 may be inserted within the hole 54, typically before the implant 10 is placed within the hole 54. The flutes 26 of the stem 14 assist in forming a cement mantle between the stem 14 and the hole 54 to receive the bone cement 56. The optional tapered configuration and blasted finish of stem 14 further enhances the bond between the implant 10 and the head 40 by providing a mechanical interface. To still further secure the implant 10 to the head 40, a suitable adhesive, such as bone cement, may be placed between the interior surface 20 and the head 40 and various coatings may be applied to the interior surface 20, such as titanium plasma, to create a bond between the interior surface 20 and the head 40.

With the implant 10 in place upon the humeral head 40, patients with inadequate rotator cuff muscles are provided with a device that permits articulation between the humerus 36 and the coracoacromial arch 48. This articulation between the humerus 36 and the coracoacromial arch 48 enhances range of motion in the patient's shoulder and reduces patient discomfort.

Figure 6:
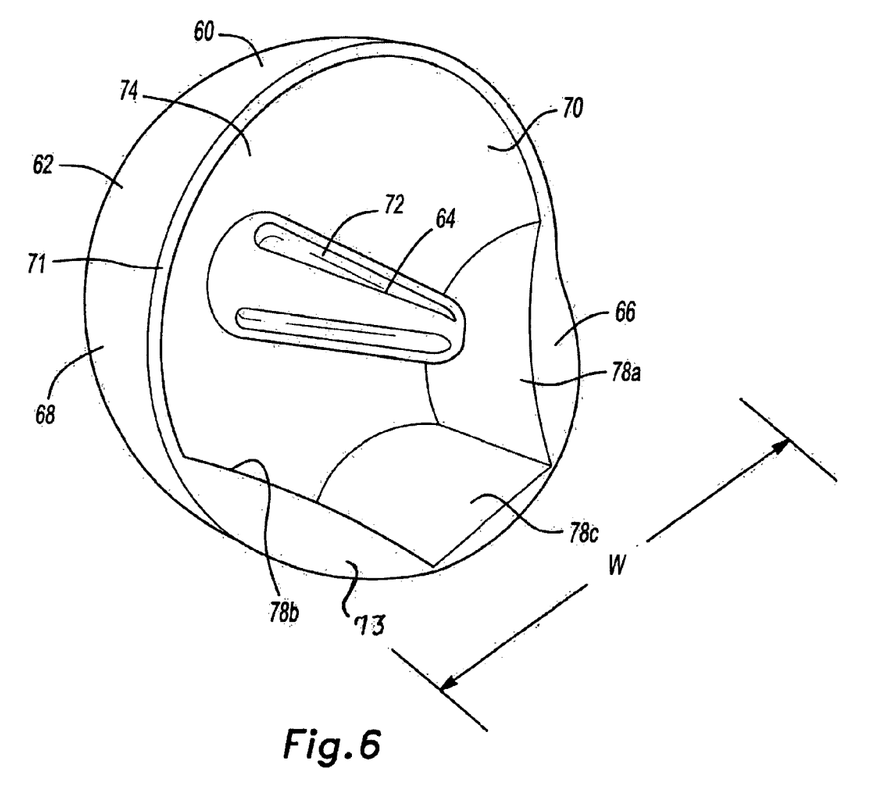
FIG. 6 represents a monolithic implant according to an embodiment of the invention.
Figure 7A:
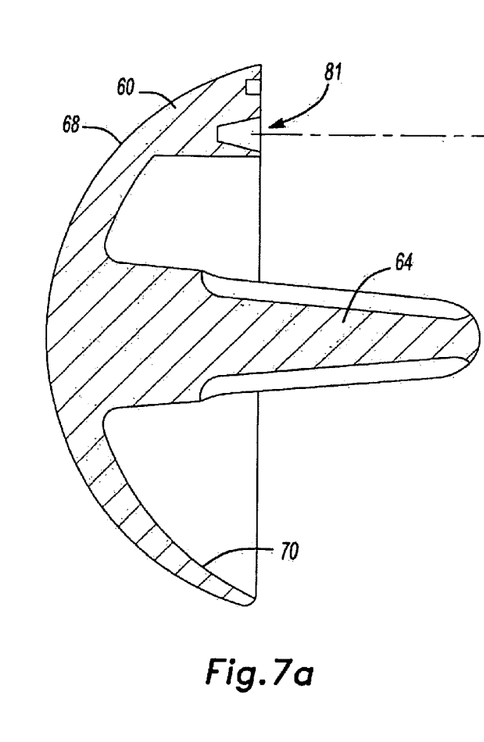
FIGS. 7A-7D represent a modular prosthetic head.
Figure 7B:
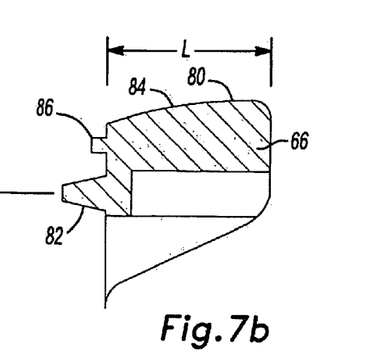
Figure 7C:
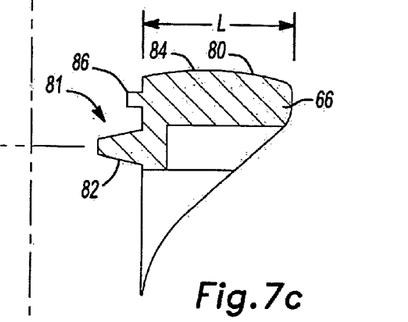
Figure 7D:
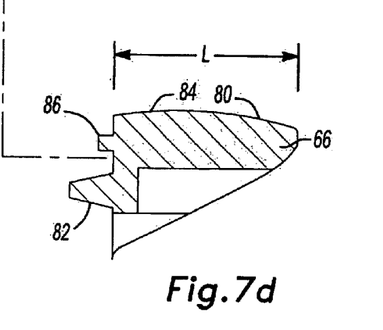

FIG. 6 represents a monolithic resurfacing implant according to the teachings of an alternate embodiment. The implant 60 includes a resurfacing head 62, an anchoring device or stem 64 and an extended bearing member 66. The head 62 has a generally spherical articulating bearing surface 68 and an interior coupling surface 70.

The stem 64 is coupled to the interior surface 70 and can have various surface features 72 to facilitate the coupling of the implant to a resected humerus. Disposed between the articulating surface 68 and the internal surface 70 of the implant 60 is a base surface 71. The base surface 71 is congruent with the base surface 73 of the bearing member 66. The internal surface 70 defines a generally spherical surface 74, which seats against a resected spherical bearing surface 76 of the humerus. Additionally, the interior surface 70 defines three flat intersecting surfaces 78A-C. Optionally, the surfaces 78A and B intersect with surface 78C at obtuse angles. The surfaces 78A-C are supported by the corresponding resected surfaces in the humeral head.

Figure 8A:
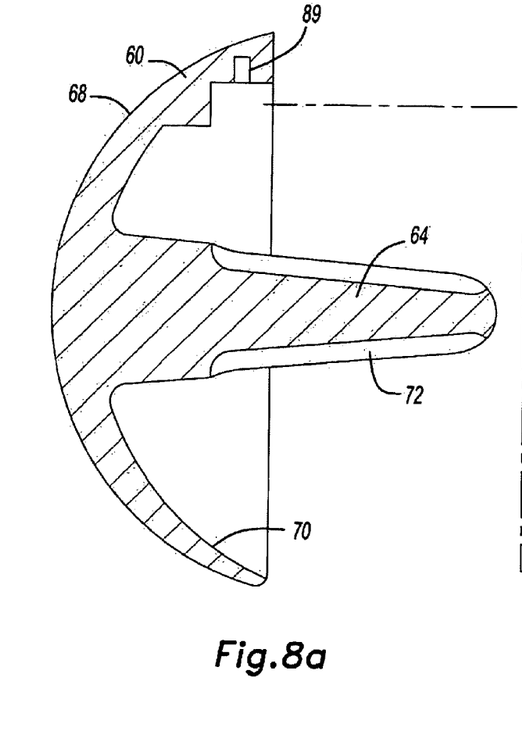
FIGS. 8A-8D represent an alternate modular prosthetic.
Figure 8B:
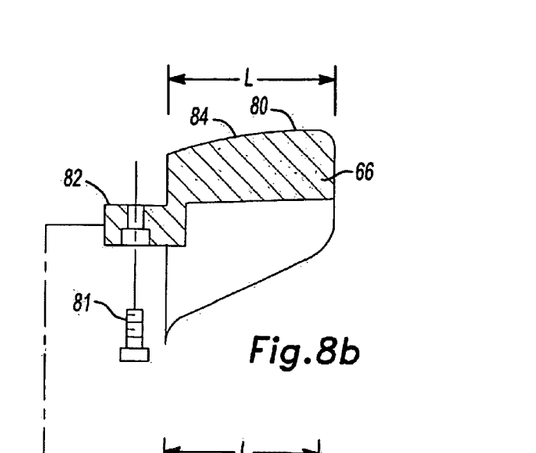
Figure 8C:
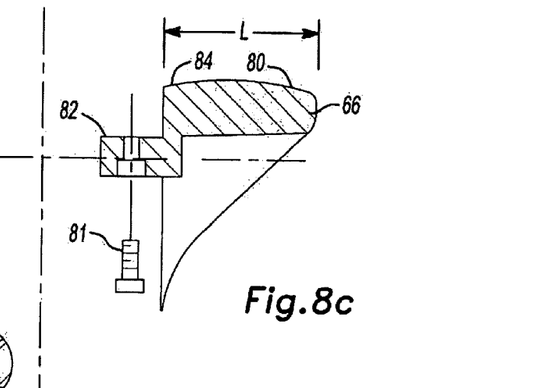
Figure 8D:
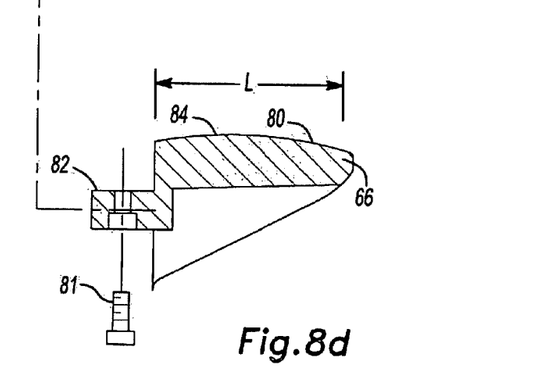

As shown in FIGS. 6, 7A-7D and 8A-8D, the extended surface can vary in radial width W and length L. As shown in FIG. 7A-8D, the extended surface can be an additional modular component 80, which can be coupled to the head using varying fixation mechanisms 81. In this regard, the fixation mechanism can optionally take the form of a pair of interference fit members, such as a Morse taper. Additionally, as shown in FIGS. 8B-8D, the fixation member can be a fastener such as a screw.

As shown in FIGS. 7A-7D, the modular component 80 has an exterior articulating surface 84 which can have varying radii of curvature which are congruent with the articulating surface 68. The modular component 80 can have a male or female Morse taper which corresponds with a complimentary structure on the interior coupling surface 70. Additionally shown is an anti-rotation member 86 in the form of a pin. As shown in FIGS. 8A-8D, the additional modular components 80 can be coupled to the implant 60 via the threaded bore 89. The threaded bore 89 can optionally be parallel or perpendicular to the fixation stem 64.

Figure 9:
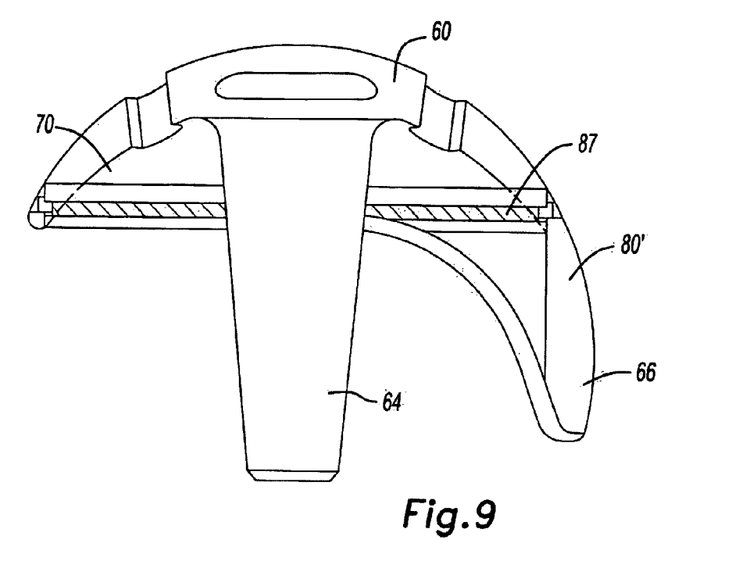
FIGS. 9 and 10 represent an alternate modular prosthetic utilizing a snap-ring fixation mechanism.
Figure 10:
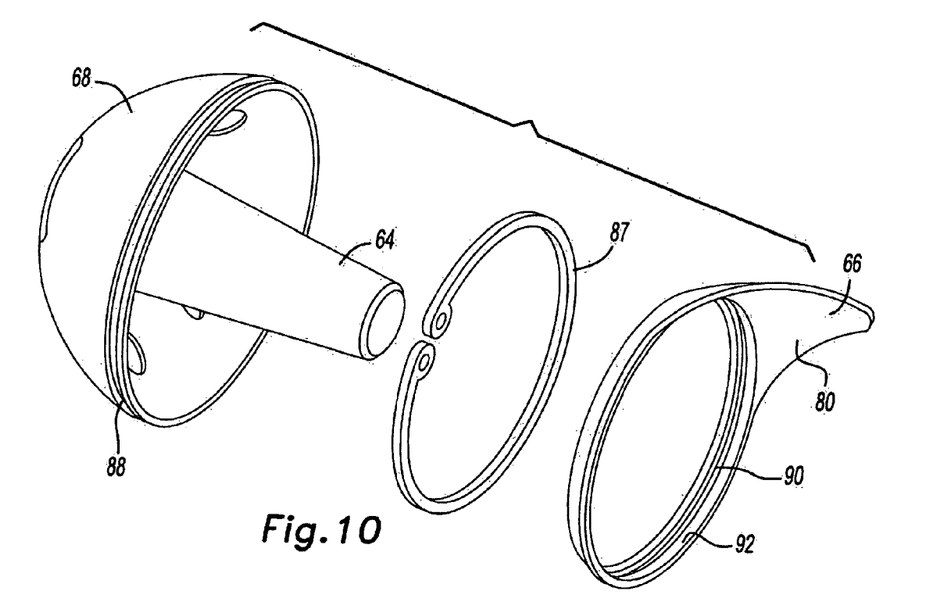

FIGS. 9 and 10 represent cross-sectional and exploded views of an alternative prosthetic. The additional modular component 80 is coupled to the interior coupling surface 70 via a ring lock 87. The ring 87 is configured to couple the annular modular component 80' using the groove 88 defined on the bearing surface 68, and a groove 90 defined on an interior surface 92 of the modular component 80'.

Figure 11:
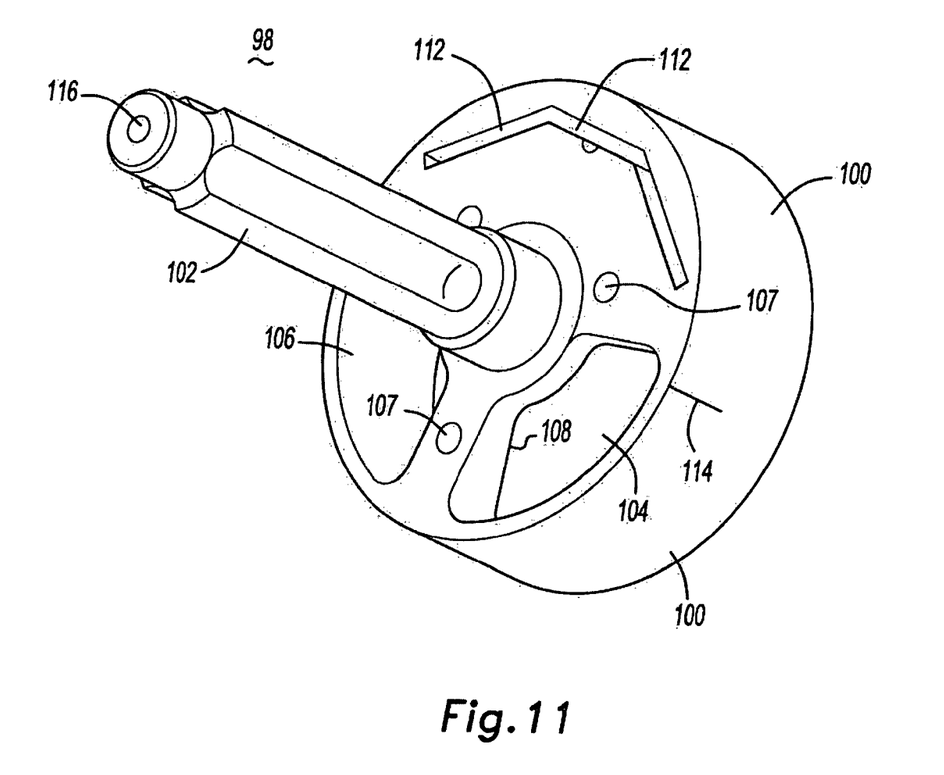
FIG. 11 represents a tool for use to implant the prosthesis shown in FIGS. 7A-10.

FIG. 11 represents a cutting guide 98 which allows for the preparation of the humerus. In this regard, the cutting guide 98 allows for the removal of tuberosities to make room for an extended implant. The cutting guide 98 has a main body 100 and a cannulated handle 102. The underside 104 of the main body has a spherical concave surface 108 that relates to the spherical radius of a spherical cutter 109 used to prepare the humerus. The guide 98 is configured to be fully seated on the resurfaced humeral head 76. A plurality of slots 106 are formed within the main body 100 for viewing the resurfaced head to determine if the guide is well seated. Additional holes 107 are formed in the guide main body 100, which accept a plurality of guide pins 110. These pins 110 prevent the rotation of the cutting guide 100 during the resection of the humerus.

Further defined in the cutting guide main body 100 are a plurality of angled cutting slots 112, which are configured to match the flats 78A-78C created on the inner surface on the resurfacing implant. In this regard, the angled slots 112 can form compound angles with respect to each other. Additional groups can be formed on an exterior peripheral surface of the main body to facilitate the removal of material. To insure the cutting guide is properly oriented, markings 114 can be formed on the outside surface of the cutting guide. These markings are intended to allow the relative rotation and placement of the cutting guide with respect to predetermined or known anatomical locations, such as the bicipital groove.

The handle 102 defines a through passage 116 or aperture, which is configured to slidably accept a Steinmann pin 118. It is envisioned that the handle can be removable from the body portion to facilitate the resection through the number of slots in the main body.

Figures 12, 13, 14, 15:
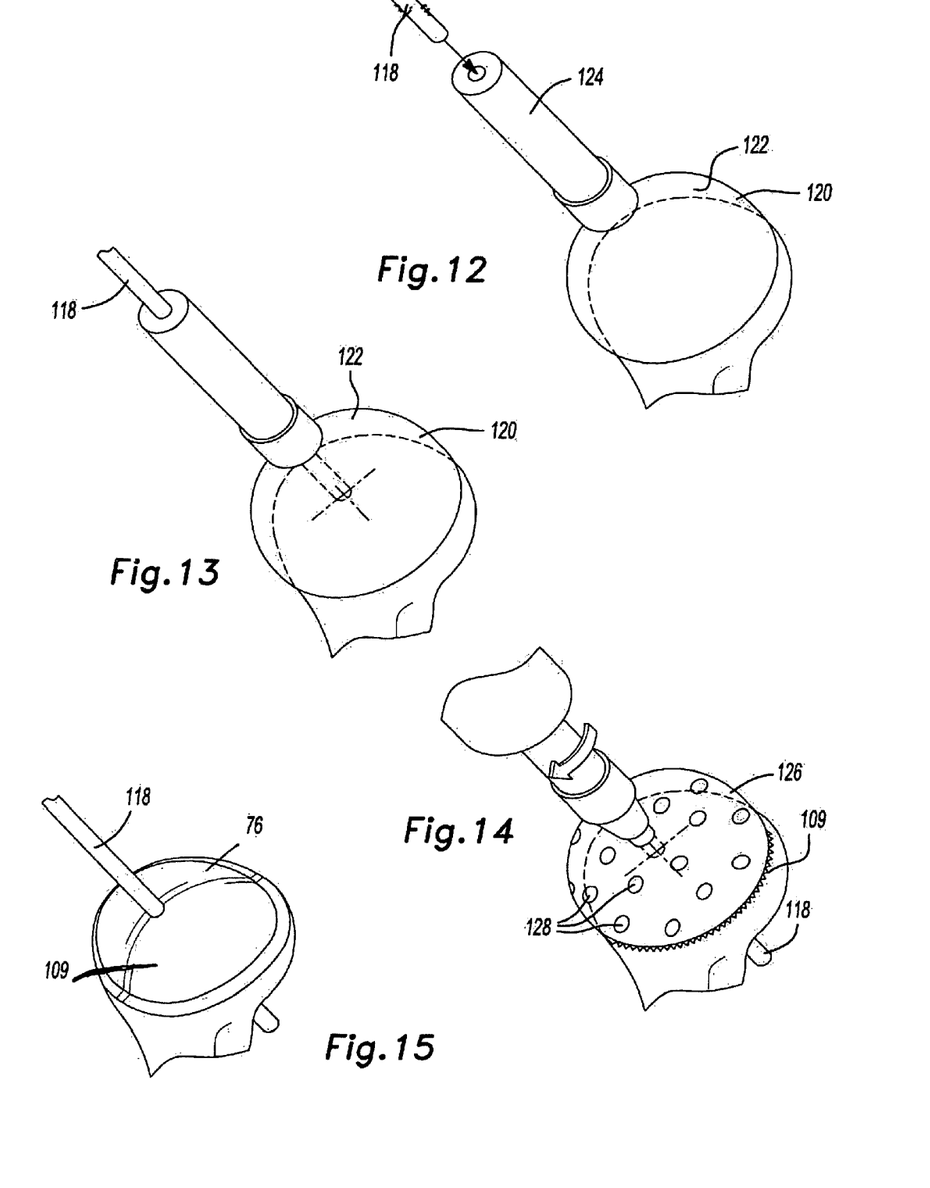
FIGS. 12-22 represent the preparation of a humerus to accept the implant shown in FIGS. 7A-10.

FIGS. 12-22 represent the preparation of the humerus to accept any of the aforementioned prosthetics. FIG. 12 represents the first step in inserting the extended articulating surface humeral resurfacing head. First, a drill guide 120 is used to locate the center of the humeral head. The drill guide 120 has a generally spherical concave inner surface 122, which is configured to conform to the generally spherical surface of the humeral head. The drilling guide has a cannulated handle 124, which is used to direct the placement of the Steinmann pin 118.

As shown in FIG. 12, the Steinmann pin 118 is disposed through the guide to mark the location of the center of the head. As also shown in FIG. 13, a spherical surface cutter 126 is placed over the Steinmann pin and used to ream the surface of the head to remove a predetermined amount of biological tissue (see FIG. 14). Optionally, the reaming continues until bone is shown coming through a plurality of holes 128 within the cutter.

Figure 16:
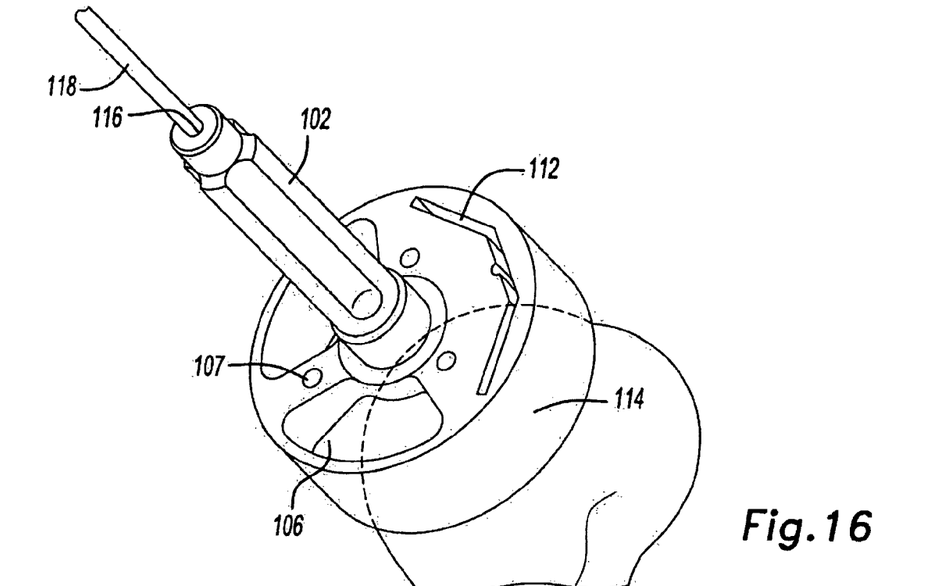
Figure 17:
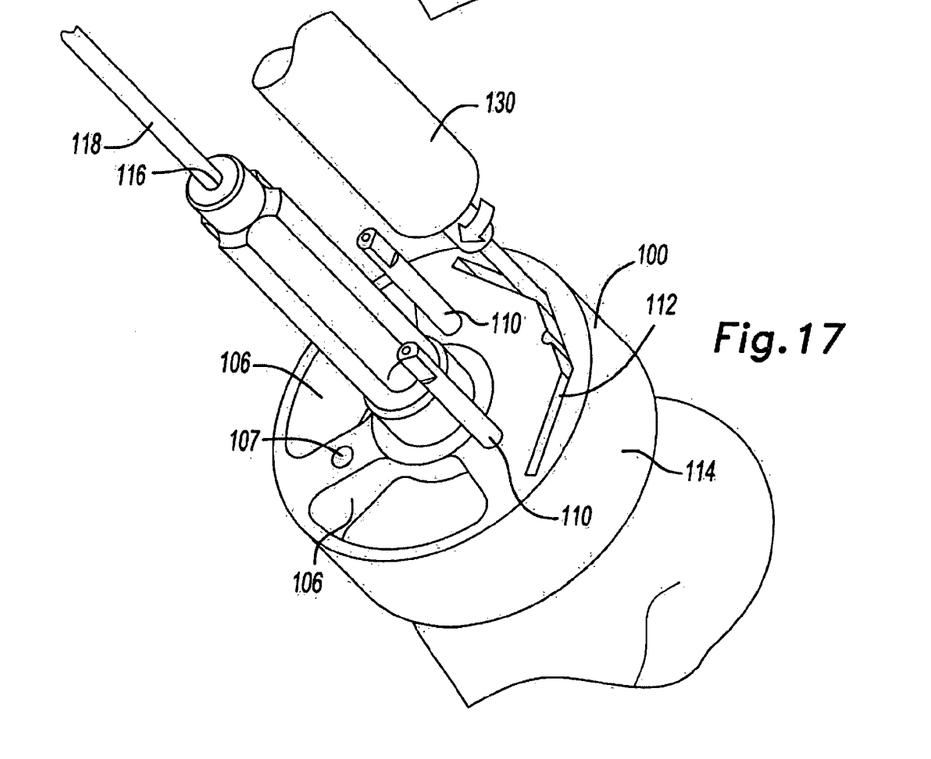
Figure 18:
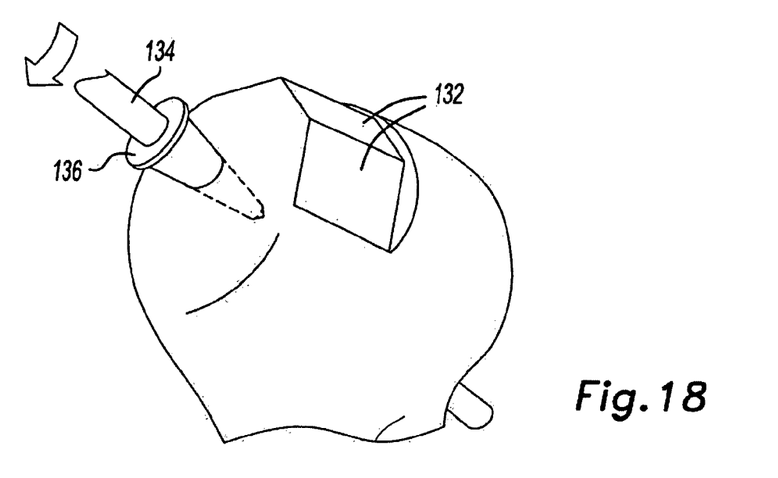
Figure 19:
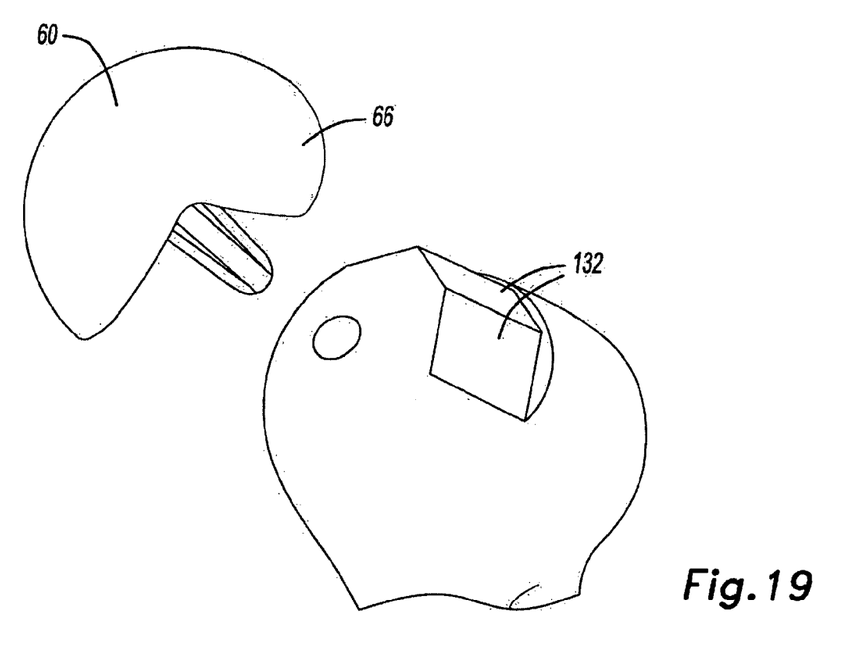

The cutting guide 100, as shown in FIG. 16, is placed over the Steinmann pin 118. The cutting guide 100 is rotated so that the marking 114 on the exterior surface of the cutting guide is lined up with the bicipital groove. The additional guide pins 110 are then placed through the guide holes 107 in the guide to prevent relative rotation of the cutting guide 100 with respect to the humerus during the resection of the humeral head.

At this point, a rotational or reciprocal cutting tool 130 is placed within the cutting grooves 112 formed in the cutting guide 100. This tool is used to form a plurality of flat surfaces 132 on the humerus. At this point, the anti-rotation pins and cutting guide are removed from the resected humerus. A spade bit 134 is placed over the Steinmann pin 118 and rotated until a stop ledge 136 touches the humeral head. Both the spade bit 134 and Steinmann pin 118 are removed from the humerus. A trial head (see FIG. 19) is then placed onto the resurfacing bone and used to check the full range of motion and correct soft tissue tensioning. Lastly, the final prosthetic is placed onto the bone and impacted into place.

Figure 20:
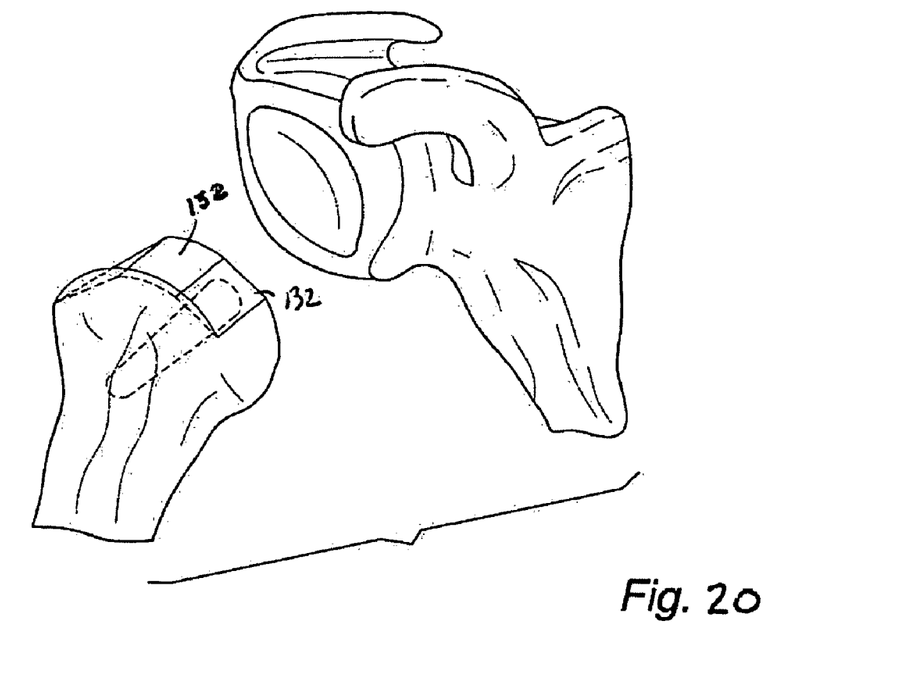
Figure 21:
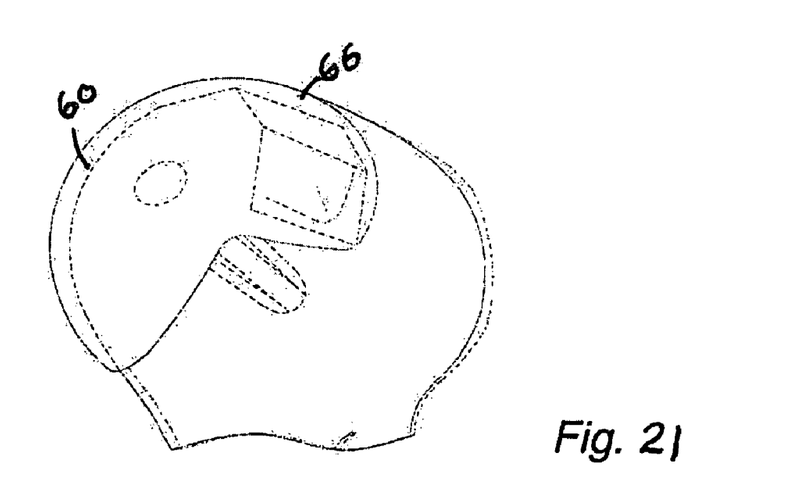
Figure 22:
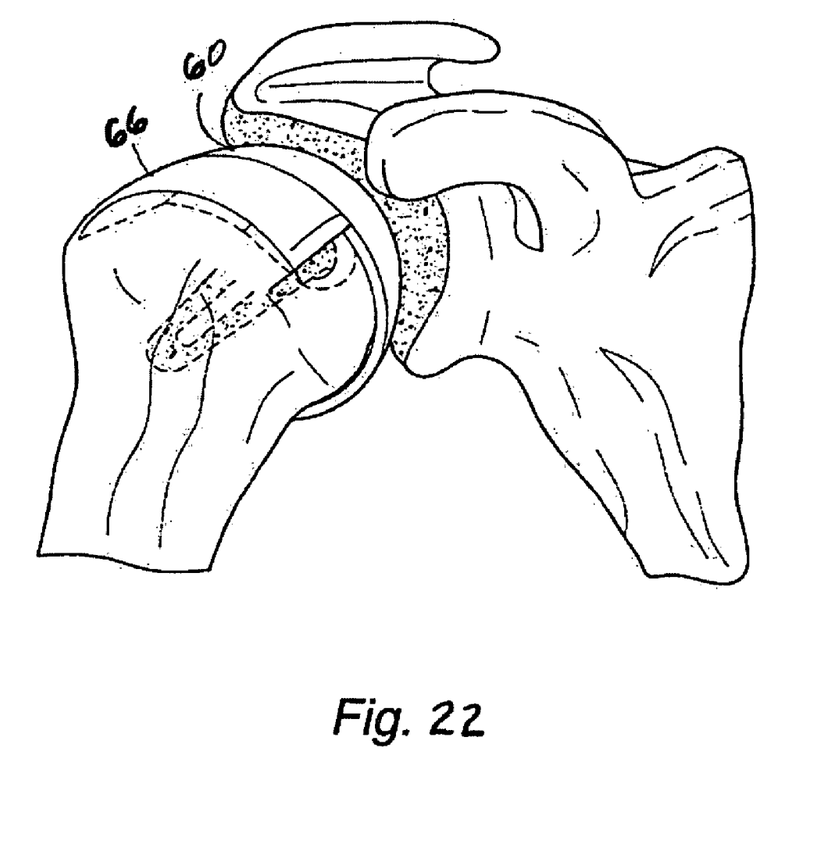

FIGS. 20-22 represent the placement of the prosthetic 60 onto the prepared humerus. As can be seen, the exterior portion 66 is positioned to allow proper articulation of the repaired joint. A trialing head 60' is positioned to the prepared humerus. The head 60 is then coupled to the resected humerus as previously described.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A monolithic humeral head resurfacing implant comprising:
    a head having:
        an exterior hemispherical articulating surface defining a terminating rim;
        an interior concave surface opposite said exterior articulating surface;
        an anchoring stem coupled to the interior concave surface and extending along an axis that extends through an axial center of the head; and
    an extended articulating surface member defining a flange axially protruding from only a portion of said terminating rim, said extended articulating surface member operable to articulate with at least one of a bone and a ligament, said extended articulating surface member has an inner bone engaging side including a plurality of intersecting flat planar bone engaging surfaces that each face the anchoring stem and an outer articulating surface that is opposite to the inner bone engaging side, the outer articulating surface is curved along substantially its entire length and is substantially congruent with said exterior hemispherical articulating surface, wherein at least two of the intersecting flat planar bone engaging surfaces define a planar "V" shaped inner surface extending generally parallel to the anchoring stem and defined only on the extended articulating surface member.

2. The implant of claim 1, wherein said implant is comprised of at least one of cobalt chrome, titanium, and a biocompatible material.

3. The implant of claim 1, wherein said extended articulating surface member defines three planar intersecting bone engaging surfaces.

4. The implant of claim 1, wherein said anchoring stem includes a first end proximate to said head and a second end distal to said head, said second end having a diameter that is smaller than said first end.

5. The implant of claim 1, wherein said exterior articulating surface is defined by a first convex surface having a first radius and said extended articulating surface member has a second convex surface having a second radius, said first and second surfaces being congruent.

6. The implant of claim 5, wherein said first radius is equal to said second radius.

7. The implant of claim 1, wherein said extended articulating surface member is located in a lateral region of said head when implanted in a patient.

8. The implant of claim 1, wherein said extended articulating surface member defines three intersecting planar interior surfaces.

9. A monolithic humeral head resurfacing implant comprising:
    a humeral head having an exterior hemispherical articulating surface and a concave interior coupling surface with an anchoring stem extending from an axial center thereof, the hemispherical articulating surface terminating at a rim at a hemispherical equator of the humeral head; and
    an extended articulating surface member defining a flange axially protruding from only a portion of the terminating rim of said humeral head, said extended articulating surface member operable to articulate with at least one element of a coracoacromial arch, said extended articulating surface member has a first, a second, and a third generally flat intersecting bone engaging surfaces that each face the anchoring stem and extend generally parallel to the anchoring stem;
    wherein the first and the second generally flat intersecting bone engaging surfaces are adjacent and define a planar "V" shaped inner surface defined only on the extended articulating surface member, and wherein said extended articulating surface member is substantially congruent with said exterior hemispherical articulating surface.

10. The implant of claim 9, wherein said anchoring stem is tapered.

11. The implant of claim 9, wherein said extended surface member is positioned at a lateral region of the implant when implanted in a patient.

12. The monolithic humeral head resurfacing implant of claim 9, wherein the extended articulating surface member includes an outer surface that is opposite to the generally flat intersecting bone engaging surfaces, the outer surface and the portion of the rim from which the extended articulating surface member protrudes each have a substantially similar degree of curvature.

13. The monolithic humeral head resurfacing implant of claim 9, wherein the third bone engaging surface intersects one of the first and the second bone engaging surfaces.

14. A monolithic humeral head resurfacing implant comprising:
    a head including:
        a hemispherical exterior articulating surface;
        a concave interior coupling surface opposite to said hemispherical exterior articulating surface;
        a rim extending between the hemispherical exterior articulating surface and the concave interior coupling surface and terminating at a hemispherical equator of the head;
    an anchoring stem that is integral with the concave interior coupling surface, extends along a longitudinal axis passing through an axial center of said head, and has a textured outer surface configured to be directly coupled to bone;
    a flange axially extending from less than an entirety of the rim, said flange is operable to articulate with at least one element of a coracoacromial arch, the flange extends generally parallel to the longitudinal axis, the flange includes a first side that faces the stem, and a second side that is opposite to the first side, said second side is substantially congruent with said hemispherical exterior articulating surface;
    the first side of the flange includes a first flat planar surface, a second flat planar surface, and a third flat planar surface that is adjacent to and between the first and second flat planar surfaces;
    the first and the second flat planar surfaces together define a "V" shape; and
    the second and the third flat planar surfaces together define a "V" shape.

* * * * *